US006284479B1

(12) United States Patent
Nichols

(10) Patent No.: US 6,284,479 B1
(45) Date of Patent: Sep. 4, 2001

(54) SUBSTITUTES FOR MODIFIED STARCH AND LATEXES IN PAPER MANUFACTURE

(75) Inventor: Scott E. Nichols, Johnston, IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/210,361

(22) Filed: Dec. 11, 1998

Related U.S. Application Data

(60) Continuation-in-part of application No. 09/008,172, filed on Jan. 16, 1998, which is a division of application No. 08/482,711, filed on Jun. 7, 1995, now abandoned, and a continuation-in-part of application No. 09/009,620, filed on Jan. 20, 1998, which is a continuation of application No. 08/485,243, filed on Jun. 7, 1995, now Pat. No. 5,712,107, and a continuation-in-part of application No. 09/007,999, filed on Jan. 16, 1998, which is a division of application No. 08/478,704, filed on Jun. 7, 1995, now abandoned.

(51) Int. Cl.$^7$ ............... C12Q 1/48; C12Q 1/00; C12Q 1/34; D21C 3/00
(52) U.S. Cl. ............ 435/15; 435/4; 435/18; 435/170; 435/278; 435/885; 435/886; 536/1.11; 536/18.5; 536/123.12; 536/124; 536/128; 162/100
(58) Field of Search ............ 435/15, 4, 18, 435/170, 278, 885, 886; 536/1.11, 18.5, 123.12, 124, 128; 162/100

(56) References Cited

U.S. PATENT DOCUMENTS 4,202,966   5/1980   Misaki et al. .............. 536/1.11
4,342,601   8/1982   Yin ........................... 536/123.12

(List continued on next page.)

FOREIGN PATENT DOCUMENTS 1122354      8/1968   (GB).
06 287 887   11/1994  (JP).
06 313 297   11/1994  (JP).
WO 94/11520  5/1994   (WO) .............. C12N/15/82
WO 95/13389  11/1994  (WO) .............. C12N/15/82

(List continued on next page.)

OTHER PUBLICATIONS

Kuramitsu, et al. "Characterization of Extracellular Glucosyltransferase Activity of *Streptococcus mutans*" Infection and Immunity; vol. 12(4): pp. 738–749; (1975).

Yamashita, et al. "Role of the *Streptococcus mutans* gtf Genes in Caries Induction in the Specific–Pathogen–Free Rat Model" Infection and Immunity; vol. 61(9); pp 3811–3817; (1993).

Kametaka, et al. "Purification and characterization of glucosyltransferase from *Streptococcus mutans* OMZ176 with chromatofocusing" Microbios; vol. 51; pp. 29–35; (1987).

Aoki, et al. "Cloning of a *Streptococcus mutans* Glucosyltransferase Gene Coding for Insoluble Glucan Synthesis" Infection and Immunity; vol. 53(3); pp. 587–595; (1986).

(List continued on next page.)

Primary Examiner—Louise N. Leary
(74) Attorney, Agent, or Firm—Pioneer Hi-Bred International, Inc.

(57) ABSTRACT

The present invention provides methods of making paper, utilizing glucans, produced by the glucosyltransferase B, C or D enzyme of the species *Streptococcus mutans,* instead of modified starches. The present glucans are functionally similar to currently utilized modified starches and are particularly useful in the coating step of paper manufacture. The present glucans also exhibit thermoplastic properties and impart gloss to the paper during the coating step.

14 Claims, 4 Drawing Sheets

U.S. PATENT DOCUMENTS

| | | | |
|---|---|---|---|
| 4,597,830 | 7/1986 | April et al. | 536/123.12 |
| 4,734,162 | 3/1988 | Ampulski | 536/123.12 |
| 5,354,424 | 10/1994 | Rha et al. | 536/123.12 |
| 5,679,880 | 10/1997 | Curtis, III et al. | 800/205 |
| 5,712,107 * | 1/1998 | Nichols | 435/15 |
| 5,712,135 | 1/1998 | Halluin et al. | 435/15 |
| 5,985,666 | 11/1999 | Loiselle et al. | 435/419 |

FOREIGN PATENT DOCUMENTS

| | | | |
|---|---|---|---|
| WO96/06173 | 8/1995 | (WO) | C12N/15/54 |
| WO 96/01904 | 1/1996 | (WO) | |
| WO 97/29186 | 2/1997 | (WO) | |
| WO 97/47806 | 12/1997 | (WO) | D21H/17/00 |
| WO 97/47808 | 12/1997 | (WO) | D21H/17/00 |

OTHER PUBLICATIONS

Shimamura, et al. "Identification of Amino Acid Residues in *Streptococcus mutans* Glucosyltransferases Influencing the Structure of the Glucan Product" *Journal Bacteriology;* vol. 176 (16); pp. 4845–4850; (1994).

Wenham, et al. "Regulation of Glucosyl– and Fructosyl-transferase Synthesis by Continuous Cultures of *Streptococcus mutans*" *J. General Microbiology;* vol. 114; pp. 117–124; (1979).

Fu, et al. "Maltodextrin Acceptor Reactions of *Streptococcus mutans* 6715 Glucosyltransferases" *Carbohydrate Research;* vol. 217; pp. 201–211; (1991).

Bhattacharjee, et al. "Formation of oc–(1→6), oc–(1→3), and oc–(1→2) Glycosidic Linkages by Dextransucrase from *Streptococcus sanguis* in Acceptor–Dependent Reactions" *Carbohydrate Research;* vol. 242; pp. 191–201; (1993).

Russell, et al. "Expression of a Gene for Glucan–binding Protein from *Streptococcus mutans* in *Escherichia coli*" *J. General Microbiology;* vol. 131; pp. 295–299; (1985).

Russell, et al. "Characterization of Glucosyltransferase Expressed from a *Streptococcus sobrinus* Gene Cloned in *Escherichia coli*" *J. General Microbiology;* vol. 133; pp. 935–944; (1987).

Shiroza, et al. "Sequence Analysis of the gtfB Gene from *Streptococcus mutans*" *Bacteriology;* vol. 169(9); pp. 4263–4270; (1987).

Müller–Röber, et al. "Inhibition of the ADP–glucose pyrophosphorylase in transgenic potatoes leads to sugar–storing tubers and influences tuber formation and expression of tuber storage protein genes" *The EMBO J.;* vol. 11(4); pp. 1229–1238; (1992).

Creech, et al., "Carbohydrate Synthesis in Maize" *Advances in Agronomy;* vol. 20; pp. 275–322; (1968).

Utsumi, et al. "Expression and Accumulation of Normal and Modified Soybean Glycinins in Potato Tubers" *Plant Science;* vol. 102; pp. 181–188; (1994).

Visser, et al. "Transformation of Homozygous Diploid Potato with an *Agrobacterium tumefacies* Binary Vector System by Adventitious Shoot Regeneration on Leaf and Stem Segments" *Plant Molecular Biology;* vol. 12; pp. 329–337; (1989).

Ebskamp, et al. "Accumulation of Fructose Polymers in Transgenic Tobacco" *Bio/Technology;* vol. 12; pp. 272–275; (1994).

Armstrong, et al. "Regeneration of Plants from Somatic Cell Cultures: Applications for in vitro Genetic Manipulation" *The Maize Handbook;* pp. 663–671; (1994).

Heiser, et al. "Starch Formulations" *Starch and Starch Products in Paper Coating;* pp. 147–162; (1990).

Honda, O., et al., "Nucleotide sequence of the *Streptococcus mutans* gtfD gene encoding the glucosyltransferase–S enzyme" J. of General Microbiology (1990) 136, 2099–2105.

Napoli et al. "Introduction of a Chimeric Chalcone Synthase Gene into Petunia Results in Reversible Co–Suppression of Homologous Genes in trans" The Plant Cell (Apr. 1990) 2, 279–289.

von Schaewen, et al. "Expression of a yeast–derived invertase in the cell wall of tobacco and Arabidopsis plants leads to accumulation of carbohydrate and inhibition of photosynthesis and strongly influences growth and phenotype of transgenic tobacco plants" The EMBO Journal (1990) vol. 9 No. 10, pp. 3033–3044.

Kossman, et al. "Transgenic plants as a tool to understand starch biosynthesis" Carbohydrate Bioengineering (1995), Petersen et al., eds., Elsevier Science, pp. 271–278.

Ueda et al. Sequence analysis of the gtfC gene from *Streptococcus mutans* GF–5, Gene. 69 (1988) pp. 101–109.

Guan, H.P. et al. "Expression of Branching Enzyme I of Maize Endosperm in *Escherichia coli*" (1994) Plant Physiology 104:1649–1453.

Hanada, et al. "Isolation and Characterization of the *Streptococcus mutans* gtfC Gene, Coding for Synthesis of Both Soluble and Insoluble Glucans" *Infection and Immunity;* vol. 56(8); pp. 1999–2005;(1988).

Creech, et al. "Carbohydrate Synthesis in Maize" *Advances in Agronomy;* vol. 20; pp.275–322; (1968).

* cited by examiner

SUBSTITUTES FOR MODIFIED STARCH AND LATEXES IN PAPER MANUFACTURE

This application is a continuation in-part of U.S. patent application Ser. No. 09/008,172 filed on Jan. 16, 1998, which is a divisional of U.S. patent application Ser. No. 08/482,711 filed on Jun. 7, 1995, now abandoned.

This application is also a continuation in-part of U.S. patent application Ser. No. 09/009,620, filed Jan. 20, 1998, which is a continuation of U.S. patent application Ser. No. 08/485,243 filed Jun. 7, 1995, which issued as U.S. Pat. No. 5,712,107.

This application is also continuation in-part of U.S. patent application Ser. No. 09/007,999 filed on Jan. 16, 1998, which is a divisional of U.S. patent application Ser. No. 08/478,704, filed on Jun. 7, 1995, now abandoned.

These applications are incorporated by reference in their entirety.

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a slurry including starch is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" contain tertiary or quaternary amines. These amino groups are added to the starch following the wet milling process.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. What limits press speed is the requirement to remove water. With a higher concentration of starch, there would be less water to remove, and the press could run at higher speed. However, higher concentrations of starch accelerate retrogradation and retrograded starch deposition onto the sheet and as noted above is unacceptable.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing. Meeting these needs would advance the state of science and industry in this area.

SUMMARY OF THE INVENTION

It is an object of the present invention to provide methods for manufacturing paper using glucans.

It is another object of the present invention to provide a method of imparting gloss during paper manufacture.

It is another object of the present invention to provide nucleic acids and polypeptides relating to substitutes for starch in paper manufacturing.

It is another object of the present invention to provide transgenic plants and plant parts containing the proteins of the present invention.

It is another object of the present invention to provide transgenic plants and plant parts containing the nucleic acids of the present invention.

Therefore, in one aspect, the present invention relates to an isolated nucleic acid comprising a member selected from the group consisting of:

(a) a polynucleotide which encodes a polypeptide of gtfb having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q;

(b) a polynucleotide which encodes a polypeptide of gtfd having changes at positions selected from the group consisting of T589D; T589E; N471D; N471D/T589D; and N471D/T589E;

(c) a polynucleotide complementary to a polynucleotide of (a) or (b).

Therefore, in another aspect, the present invention relates to an isolated protein comprising a member selected from the group consisting of:

(a) a polypeptide comprising at least 20 contiguous amino acids in a polypeptide of gtfb having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169AY170A/Y171A; and K779Q (b) a polypeptide comprising at least 20 contiguous amino acids in a polypeptide of gtfd having changes at positions selected from the group consisting of T589D; T589E; N471D; N471D/T589D; and N471D/T589E;

(c) a polypeptide comprising at least 50% sequence identity to the nucleic acid of claim 1, wherein the % sequence identity is based on the entire sequence and is determined by GAP analysis using Gap Weight of 12 and Length Weight of 4;

(d) a polypeptide encoded by the nucleic acid of claim 27;

(e) a polypeptide encoded by the nucleic acid of gtfb having changes at positions selected from the group consisting of; I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q; and (f) a polypeptide encoded by the nucleic acid of gtfd having changes at positions selected from the group consisting of T589D; T589E; N471D; N471D/T589D; and N471D/T589E.

DETAILED DESCRIPTION OF THE INVENTION

Figure 1A:
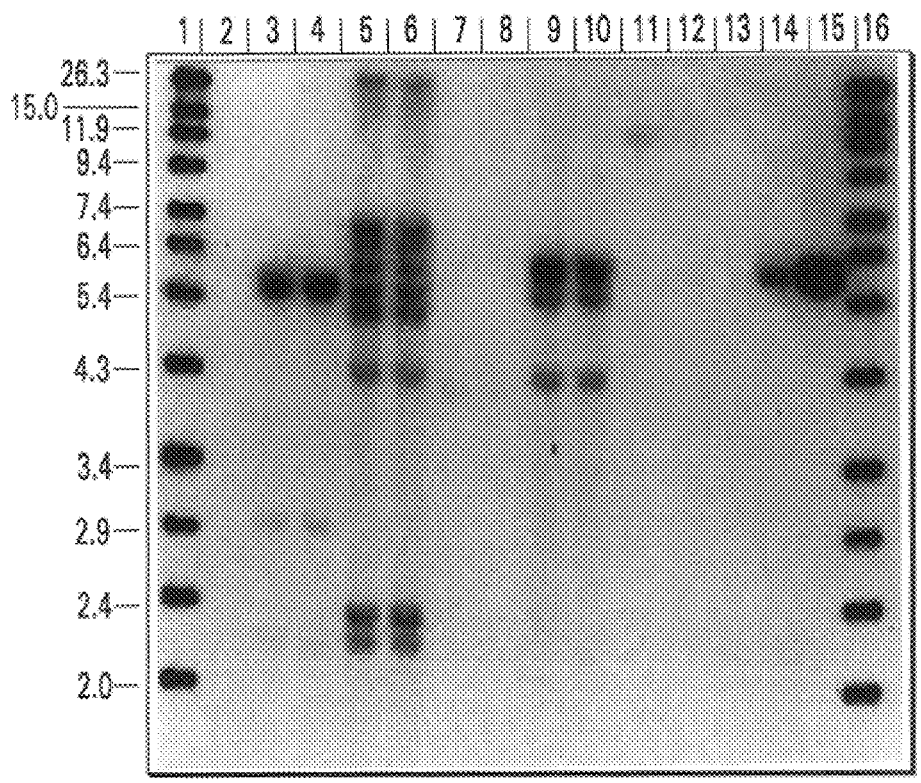
FIG. 1. Southern blot of gtfc transgenic plants-PTU analysis.
Figure 1B:
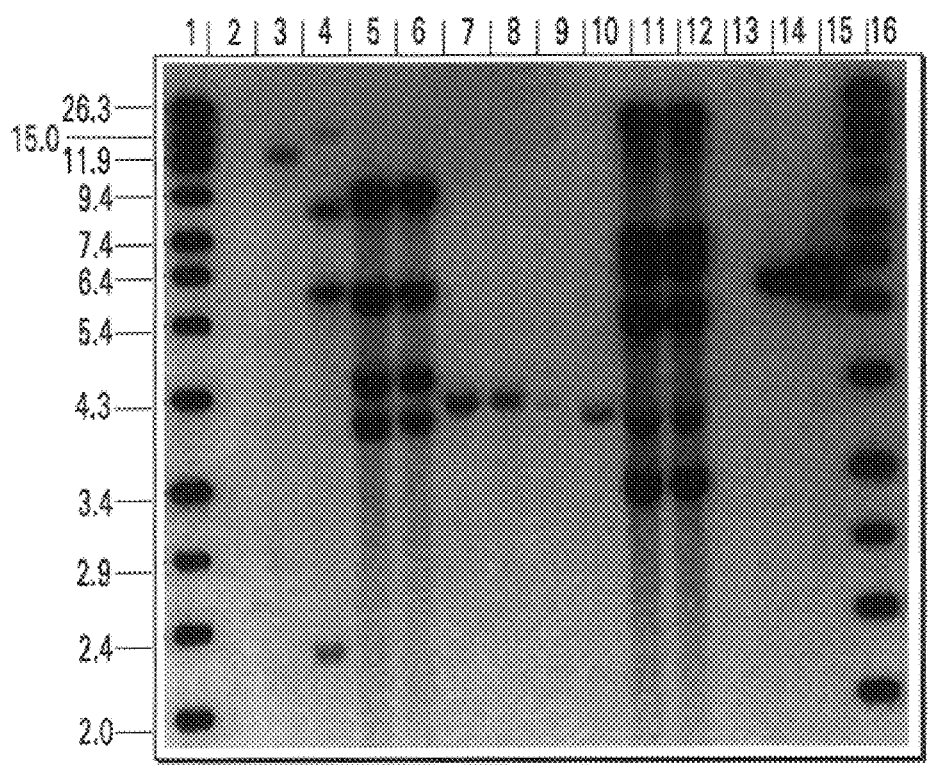
Figure 2A:
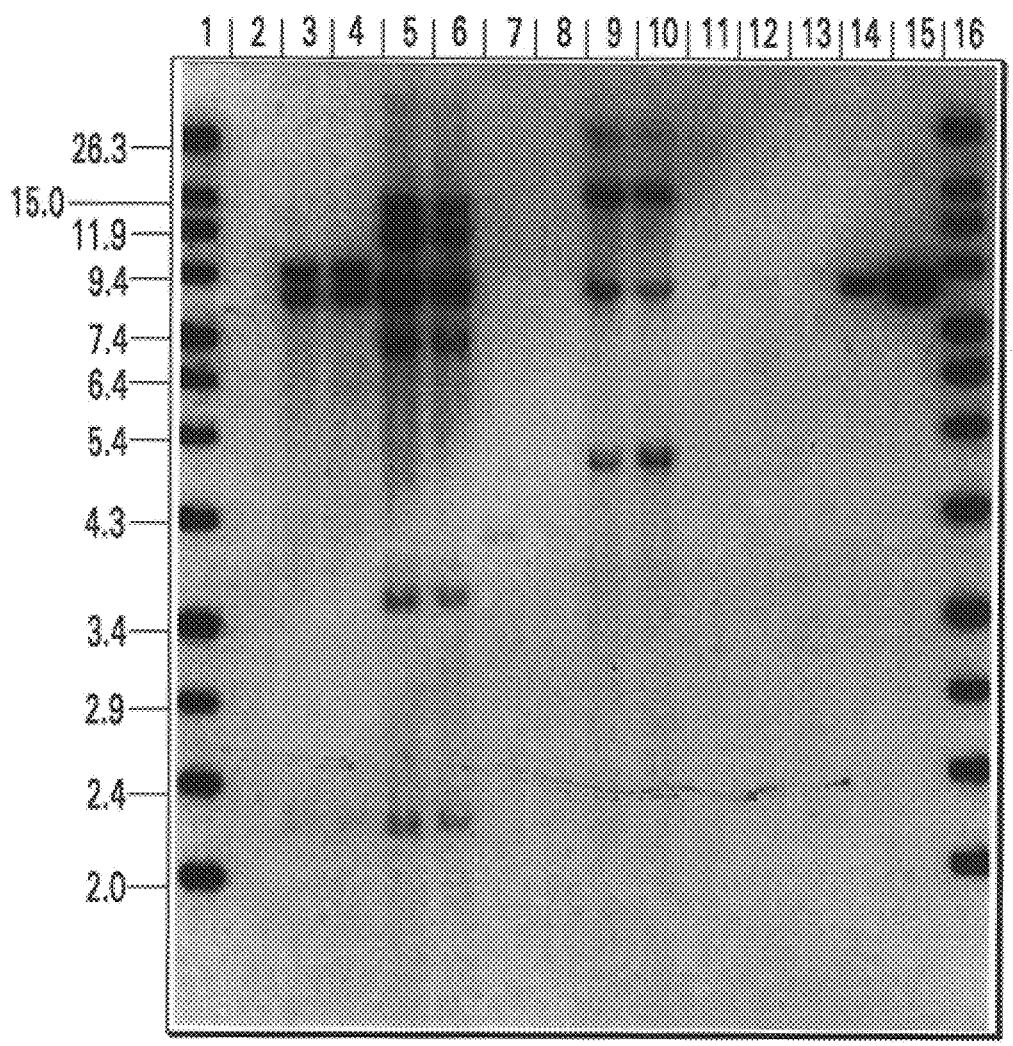
FIG. 2. Southern blot of gtfc transgenic plants-integration analysis.
Figure 2B:
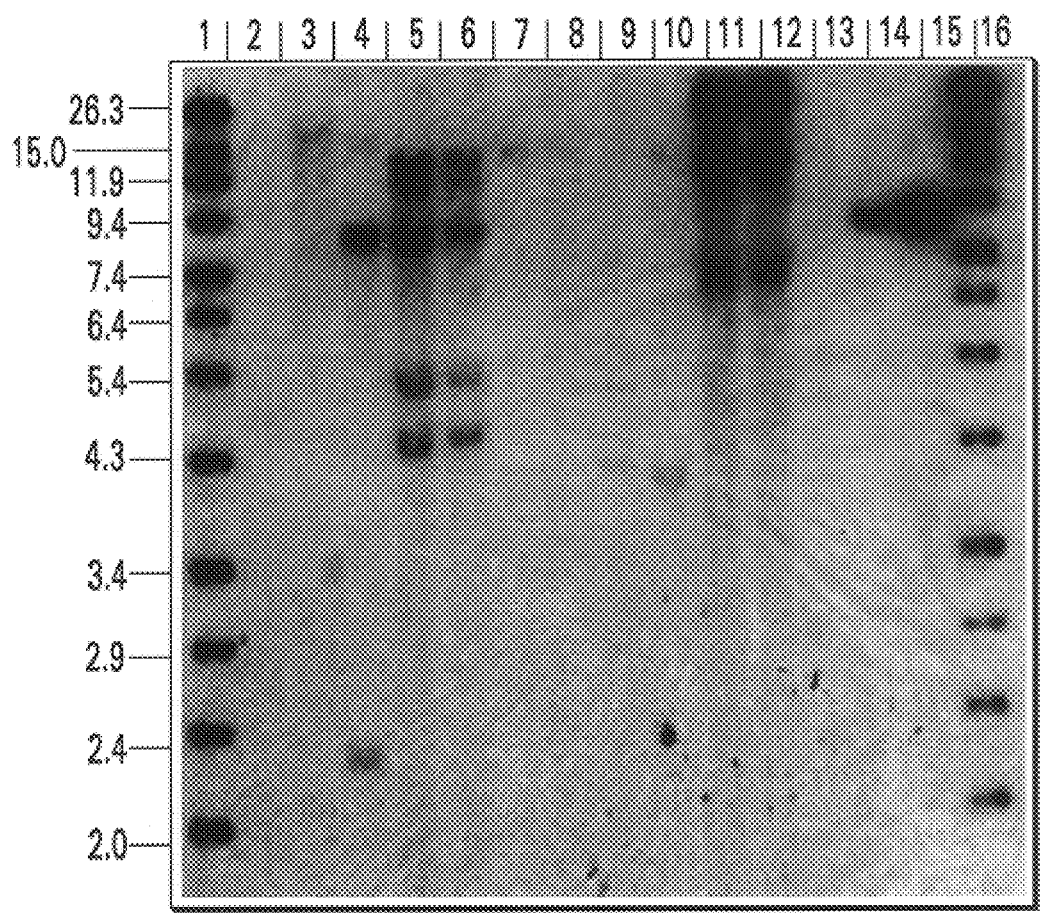
Figure 3:
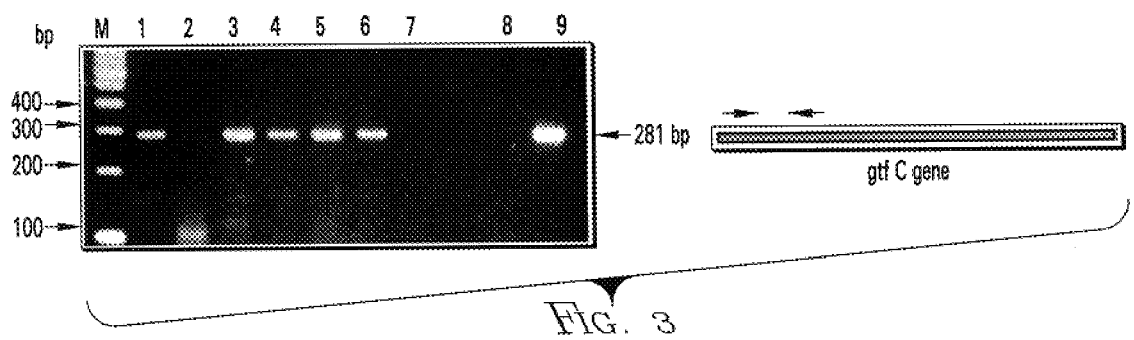
FIG. 3. RT-PCR of gtfc transgenic plants

Seq ID No. 1—a gtfb cDNA sequence
Seq ID No. 2—the GTFB protein sequence encoded by Seq ID No. 1
Seq ID No. 3—a gtfc cDNA sequence
Seq ID No. 4—the GTFC protein sequence encoded by Seq ID No. 3
Seq ID No. 5—a gtfd cDNA sequence
Seq ID No. 6—the GTFD protein sequence encoded by Seq ID No. 5

The present invention provides glucans which can be used as substitutes for and additions to modified starch and latexes in paper manufacture. The glucans of the present invention are produced by the glucosyltransferase B ("GTF B"), glucosyltransferase C ("GTF C"), and glucosyltransferase D ("GTF D") enzymes, encoded by genes, alleles and mutations of gtfb, gtfc and gtfd. The present invention also includes gtf genes and GTF proteins with sequence identity, fragments, deletions, truncations, insertions and substitutions of the GTF proteins and genes of the species *Streptococcus mutans* that are functionally similar to the modified starch currently used in paper manufacture. The present glucans also exhibit similar physical properties to thermoplastic molecules currently used in the coating step during paper manufacture.

The present invention also provides methods of making paper utilizing the present glucans, input materials that are produced biologically. Thus, the present methods are more cost-effective and environmentally friendly than current methods, which require input materials that produce chemical effluents.

DEFINITIONS

As used herein "glucan" means a glucose polymer having linkages that are predominantly (1→3), (1→6) with branch points occurring at (1→3,6). Minor linkages at (1→2) and (1→4).

As used herein "amyloplast" means starch accumulating organelle in plant storage tissue.

As used herein, "vacuole" means the cellular compartment bounded by the tonoplast membrane.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "polypeptide" means proteins, protein fragments, modified proteins, amino acid sequences and synthetic amino acid sequences. The polypeptide can be glycosylated or not.

As used herein, "plant" includes but is not limited to plant cells, plant tissue and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid. Alternatively, fragments of a nucleotide sequence that are useful as hybridization probes generally do not encode fragment proteins retaining biological activity. Thus, fragments of a nucleotide sequence are generally greater than 10 nucleotides, preferably at least 20 nucleotides and up to the entire nucleotide sequence encoding the proteins of the invention. Generally the probes are less than 1000 nucleotides and preferably less than 500 nucleotides. Fragments of the invention include antisense sequences used to decrease expression of the inventive genes. Such antisense fragments may vary in length ranging from at least about 20 nucleotides, about 50 nucleotides, about 100 nucleotides, up to and including the entire coding sequence.

By "variants" is intended substantially similar sequences.

Generally, nucleic acid sequence variants of the invention will have at least 70%, preferably 80%, more preferably at least 90% and most preferably at least 95% sequence identity to the native nucleotide sequence as determined by homology algorithms such as described below.

Generally, polypeptide sequence variants of the invention will have at least about 80%, preferably at least about 90%, and more preferably at least about 95% sequence identity to the native protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., U.S.A.; the CLUSTAL program is well described by Higgins and Sharp, *Gene* 73:237–244 (1988); Higgins and Sharp, *CABIOS* 5:151–153 (1989); Corpet, et al., *Nucleic Acids Research* 16:10881–90 (1988); Huang, et al., *Computer Applications in the Biosciences* 8:155–65 (1992), and Pearson, et al, *Methods in Molecular Biology* 24:307–331 (1994).

Also useful are the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information (http://www.ncbi.nlm.nih.gov/).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-lnterscience, New York (1995).

By "functionally equivalent" is intended that the sequence of the variant defines a polynucleotide that encodes a protein having substantially the same biological effect as the native protein of interest.

The wild type nucleic acids encoding GTF B, GTF C and GTF D enzymes are useful in producing glucans according to the present invention. The glucans produced are particularly useful as substitutes for modified starches in the coating step of paper manufacture. The present glucans are also useful as substitutes for thermoplastic molecules such as latex (e.g. styrene butadiene). The subject glucans impact a high gloss finish on the paper and increase the ability of the paper to take on dyes and inks and improves the resolution in general on the printed sheet.

*Streptococcus mutans* is a species that is endogenous to the oral cavity and colonizes tooth enamel. See e.g. Kuramitsu, et al., "Characterization of Extracellular Glucosyl Transferase Activity of *Streptococcus-mutans,*" *Infect. Immun.;* Vol. 12(4); pp. 738–749; (1975); and Yamashita, et al., "Role of the *Streptococcus-Mutans-gtf* Genes in Caries Induction in the Specific-Pathogen-Free Rat Model," *Infect. Immun.;* Vol. 61(9); pp. 3811–3817; (1993); both incorporated herein their entirety by reference. *Streptococcus mutans* species secrete the glucosyltransferase B, C and D ("GTF B, C and D") enzymes, which utilizes dietary sucrose to make a variety of extracellular glucans. See e.g. Shiroza, et al., "Sequence Analysis of the gtfb Gene from *Streptococcus mutans,*" *J. Bacteriol.;* Vol. 169(9); pp. 4263–4270; (1987); Hanada, et al., "Isolation and Characterization of the *Streptococcus mutans gtfc* Gene, Coding for Synthesis of Both Soluble and Insoluble Glucans," *Infect. Immun.;* Vol. 56(8); pp. 1999–2005; (1988); Honda et al., "Nucleotide Sequence of the *Streptococcus mutans gtfD* Gene Encoding the Glucosyltransferase-S Enzyme" J.Gen. Microbiol. Vol. 136 pp 2099–2105; and Kametaka, et al., "Purification and Characterization of Glucosyltransferase from *Streptococcus-mutans* OMZ176 with Chromatofocusing," *Microbios;* Vol. 51(206); pp. 29–36; (1978); both incorporated herein in its entirety by references.

*Streptococcus sobrinus* is a serotype of *Streptococcus mutans* and included in this invention. One of skill in the art will recognize that other glucans can be utilized in the present invention such as *S. sanguis, S. rattus. S. milleri, S. bovis, S. oralis, S. gordonii* and *S. salivarius.*

Both soluble and insoluble glucans are synthesized, and the proteins responsible have been isolated and characterized. See e.g. Aoki, et al., "Cloning of a *Streptococcus-mutans* Glucosyltransferase Gene Coding for Insoluble Glucan Synthesis" *Infect. Immun.,* Vol. 53 (3); pp. 587–594; (1986); Shimamura, et al., "Identification of Amino Acid Residues in *Streptococcus mutans* Glucosyltransferases Influencing the Structure of the Glucan Produced," *J. Bacteriol.;* Vol. 176(16); pp. 4845–50; (1994); and Kametaka, et al., "Purification and Characterization of Glucosyltransferase from *Streptococcus-mutans* OMZ176 with Chromatofocusing," *Microbios;* Vol. 51 (206); pp. 29–36; (1987); all incorporated herein their entirety by reference.

The proteins involved are large (~155 kDa) and catalyze the group transfer of the glucosyl portion of sucrose to an acceptor glucan predominantly via (1→3) and (1→6) linkages. See e.g. Wenham, et al., "Regulation of Glucosyl Transferase and Fructosyl Transferase Synthesis by Continuous Cultures of *Streptococcus-mutans,*" *J. Gen Microbiol.;* Vol. 114 (Part 1); pp. 117–124; (1979); and Fu, et al., "Maltodextrin Acceptor Reactions of *Streptococcus-mutans* 6715 glucosyltransferases," *Carbohydr. Res.;* Vol. 217; pp. 210–211; (1991); and Bhattacharjee, et al., "Formation of Alpha-(1→6), Alpha-(1→3), and Alpha (1→2) Glycosidic Linkages by Dextransucrase from *Streptococcus Sanguis* in Acceptor-Dependent Reactions," *Carbohydr. Res.,* Vol. 242; pp. 191–201; (1993); all incorporated herein their entirety by reference.

The genes involved in glucan synthesis have been isolated and sequenced. See Shimamura, et al., cited hereinabove and Russell, et al., "Expression of a Gene for Glucan-binding Protein from *Streptococcus-mutans* in *Eschericia-coli,*" *J Gen. Microbiol.;* Vol. 131(2); pp. 295–300; (1985); Russell, et al., "Characterization of Glucosyltransferase Expressed from a *Streptococcus-Sobrinus* Gene Cloned in *Escherichia-coli,*" *J. Gen. Microbiol.;* Vol. 133(4); pp. 935–944; (1987); and Shiroza, et al., "Sequence Analysis of the gtfb Gene from *Streptococcus mutans,*" *J Bacteriol.;* Vol. 169(9); pp. 4263–4270; (1987); all incorporated herein in their entirety by reference. Ueda et al, "Sequence Analysis of the gtfc Gene from *Streptococcus mutans* GF-S, Gene 69 (1988) pp. 101–109.

The structure of the glucans produced by the GTF B, C and D enzymes is quite heterogeneous with respect to the proportions of (1→3), (1→6) and (1→3,6) branches present in any given glucan. Transformation of genes that encode naturally occurring GTF B, GTF C or GTF Ds into plants, such as maize, provides novel compositions.

GTF B, GTF C or GTF D enzyme expression or activity in the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch-starch interactions that lead to helix formation is diminished. A paste made from the mixed polymers is less prone to retrogradation as a result. This should be especially true in the starch accumulation mutants envisioned as transformation targets where the relative proportion of starch is reduced.

In a highly preferred embodiment of the present invention, maize lines deficient in starch biosynthesis are transformed with gtfb, gtfc and gtfc genes. Such lines may be like naturally occurring maize mutants (i.e. sh$_2$, bt$_2$, bt$_1$). Transgenic maize may be engineered so as to accumulate lower amounts of starch in the endosperm than does wild type maize See e.g. Muller-Röber, et al., "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal;* Vol. 11(4); pp. 1229–1238; (1992); and Creech, "Carbohydrate Synthesis in Maize," *Advances in Agronomy;* Vol. 20; pp. 275–322; (1968); both incorporated herein in their entirety by reference. Naturally occurring or genetically engineered maize mutants may be identified by molecular techniques known in the art. Such as antisense, mutation, aptamer or other ways known in the art. Putative gene candidates involved in reduced starch biosynthesis are phosphoglucomutase, starch synthase, starch branching enzymes and others well know in the art.

Glucans produced in transgenic maize by the expression of GTF B, GTF C and GTF D enzymes can function in paper processing without chemical modification, as required of starch. The polymer solution consequently has altered rheological properties and is less prone to retrogradation compared to starch. The glucans are branched and irregular and able to supplant modified starches with comparable or superior efficacy. They do not require any costly chemical modification as does starch. For coating applications, the present glucans exhibit thermoplastic properties in addition to the above advantages.

The nomenclature used below to define the mutant GTF B and GTF D enzymes is as follows: the amino acid position in the polypeptide chain is determined using the start methionine as position 1; the first letter refers to the amino acid in the wild type enzyme; the second letter refers to the amino acid in the mutated enzyme; and enzymes with multiple mutations have each mutation separated by 1.

The wild type GTF B and GTF D and mutants thereof useful in producing glucans according to the present invention are provided below. The following code is employed:

| Amino Acid | One-letter Symbol |
| --- | --- |
| Alanine | A |
| Asparagine | N |
| Aspartic Acid | D |
| Glutamine | Q |
| Glutamic Acid | E |
| Isoleucine | I |
| Lysine | K |
| Threonine | T |
| Tyrosine | Y |
| Valine | V |

The mutant GTF B enzyme used to produce glucans for paper coating is preferably selected from the group consisting of wild type; I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q.

The mutant GTF B enzyme used to produce glucans for paper coating is more preferably selected from the group consisting of I448V; K1014T; D567T/D571K/K1014T; I448V/D457N/D567T/D571K/K779Q/K1014T; and Y169A/Y170A/Y171A.

The mutant GTF B enzyme used to produce glucans for paper coating is even more preferably selected from the group consisting of K1014T; I448V/D457N/D567T/D571K/K779Q/K1014T; and Y169A/Y170A/Y171A.

The mutant GTF B enzyme used to produce glucans for paper coating is most preferably I448V/D457N/D567T/D571K/K779Q/K1014T; or Y169A/Y170A/Y171A.

The mutant GTF B enzyme used to produce glucans for paper sizing is preferably selected from the group consisting of I448V; D457N; D567T; K779Q; K1014T; D457N/D567T; D457N/D571K; D567T/D571K and D567T/D571K/K1014T.

The mutant GTF B enzyme used to produce glucans for paper sizing is more preferably selected from the group consisting of I448V; D457N: K779Q; D567T/D571K; and D567T/D571K/K1014T.

The mutant GTF B enzyme used to produce glucans for paper sizing is most preferably I448V.

The mutant GTF D enzymes used to produce glucans for paper coating are preferably selected from the group consisting of; the wild type of the enzyme; T589D; T589E; N471D; N471D/T589D; and N471D/T589E; more preferably from the group consisting of the wild type; N471D; N471D/T589D; and N471D/T589E; even more preferably from the group consisting of the wild type and N471D. The wild type of the enzyme is the most preferred.

The mutant GTF D enzymes used to produce glucans for paper sizing are preferably selected from the group consisting of the wild type of the enzyme; T589D; T589E; N471D; N471D/T589D; and N471D/T589E; more preferably from the group consisting of N471D; N471D/T589D; and N471D/T589E; most preferably N471D.

NUCLEIC ACIDS

The glucans of the present invention are produced by the glucosyltransferase B ("GTF B"), glucosyltransferase C ("GTF C"), and glucosyltransferase D ("GTF D") enzymes, encoded by genes, alleles and mutations of gtfb, gtfc and gtfd. The present invention also includes gtf genes and GTF proteins with "sequence identity, fragments, deletions, truncations, insertions and substitutions of the GTF proteins and genes of the species Streptococcus mutans that are functionally similar to the modified starch currently used in paper manufacture. For example see "Glucosyltransferase gene polymorphism among Streptococcus mutans strains" CHIA-J-S; HSU-T-Y; TENG-L-J; CHEN-J-Y; HAHN-L-J; YANG-C-S, INFECTION AND IMMUNITY 59(5): 1656–1660, 1991 and "Analysis of a DNA polymorphic region in the gtfB and gtfC genes of Streptococcus mutans" CHIA-J-S; LIN-S-W; HSU-T-Y; CHEN-J-Y; KWAN-H-W; YANG-C-S, INFECTION AND IMMUNITY 61(4): 1563–1566, 1993.

Most deletions, insertions and substitutions of the protein sequence are not expected to produce radical changes in the characteristics of the protein. However, when it is difficult to predict the exact effect of the substitution, deletion or insertion in advance of doing so, one skilled in the art will appreciate that the effect will be evaluated by routine screening assays such as the proteins and genes of the invention may be altered in various ways, as indicated above, and methods for such manipulations are generally known in the art. See, for example, Kunkel, T. (1985) Proc. Natl. Acad. Sci. U.S.A. 82:488–492: Kunkel et al. (1987) Methods in Enzymol. 154:367–382: U.S. Pat. No. 4,873,192; Walker and Gaastra (eds.) Techniques in Molecular Biology, MacMillan Publishing Company, NY (1983). It is further recognized that component polypeptides or fragments of the proteins may be produced which retain activity. These fragments include truncated sequences, as well as N-terminal, C-terminal, internal and internally deleted amino acid sequences of the proteins.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, canola, alfalfa, potato, sugar beet or cassava.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), DIRECTED MUTAGENESIS: A Practical approach, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alters, adds or deletes a single amino acid or a small percentage of amino acids in the encoded sequence is a "conservatively modified variant" where the alteration results in the substitution of an amino acid with a chemically similar amino acid. When the nucleic acid is prepared or altered synthetically, advantage can be taken of known codon preferences of the intended host.

The present invention also includes nucleic acids produced by DNA sequence shuffling of the inventive polynucleotides to obtain a desired characteristic. Sequence shuffling is described in PCT publication No. 96/19256. See also, Zhang, J.-H., et al, Proc. Natl. Acad. Sci. U.S.A. 94:4504–4509 (1997).

The present invention also includes the use of 5' and/or 3' untranslated regions (UTR) regions for modulation of translation of heterologous coding sequences. Positive sequence motifs include translational initiation consensus sequences (Kozak, Nucleic Acids Res. 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12:387–395 (1984)) or MacVector 4.1 (Eastman Kodak Co., New Haven, Conn.).

For example, the inventive nucleic acids can be optimized for enhanced expression in plants of interest. See, for example, EPA0359472; WO91/16432; Perlak et al. (1991) *Proc. Nati. Acad. Sci. U.S.A.* 88:3324–3328; and Murray et al. (1989) *Nucleic Acids Res.* 17:477–498. In this manner, the genes can be synthesized utilizing plant-preferred codons. See, for example, Murray et al. (1989) *Nucleic Acids Res.* 17:477–498, the disclosure of which is incorporated herein by reference.

The present invention provides subsequences comprising isolated nucleic acids containing at least 16 contiguous bases of the inventive sequences. For example the isolated nucleic acid includes those comprising at least 16, 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.* 15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. U.S.A.* 88:1943–1947 (1991); U.S. Pat. Nos. 5,482,685 and 5,637,685; and Soares et al., *Proc. Natl. Acad. Sci. U.S.A.* 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique* 3(2):58–63 (1991); Sive and St. John, *Nucl. Acids Res.* 16(22):10937 (1988); *Current Protocols in Molecular Biology*, Ausubel, et al., Eds., Greene Publishing and Wiley-Interscience, New York (1995); and, Swaroop et al., *Nucl. Acids Res.* 19)8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology,* Chapter 2, Ausubel, et al., Eds., Greene Publishing and Wiley-lnterscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997).

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.* 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The glucans of the present invention are preferably produced in transgenic maize, potato, sugar beet, cassava, sweet potato, rye, barley, wheat, sorghum, oats, millet, triticale, sugarcane and rice. More preferably, the present glucans are produced in maize, potato, sugar beet, sugarcane, cassava, and sweet potato. Even more preferably, the present glucans are produced in maize, sugar beet and potato. Most preferably, the present glucans are produced in maize.

The production of the present glucans in transgenic plants is performed according to methods of transformation that are well known in the art, and thus constitute no part of this invention. The compounds of the present invention are synthesized by insertion of an expression cassette containing a synthetic gene which, when transcribed and translated, yields a GTF enzyme that produces the desired glucans. Such empty expression cassettes, providing appropriate regulatory sequences for plant expression of the desired sequence, are also well-known, and the nucleotide sequence for the gene, either RNA or DNA, can readily be derived from the amino acid sequence for the protein using standard texts and the references provided. The above-mentioned genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes that encode for the present enzymes can be inserted into an appropriate expression cassette and introduced into cells of a plant species. Thus, an especially preferred embodiment of this method involves inserting into the genome of the plant a DNA sequence coding for a mutant or wild type enzyme in proper reading frame, together with transcription promoter and initiator sequences active in the plant. Transcription and translation of the DNA sequence under control of the regulatory sequences causes expression of the protein sequence at levels that provide an elevated amount of the protein in the tissues of the plant.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The gene of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

EXPRESSION CASSETTES

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook, et al.; *Molecular Cloning: A Laboratory Manual;* Cold Spring Harbor, N.Y.; (1989); Gelvin, et al.; *Plant Molecular Biology Manual* (1990); *Plant Biotechnology: Commercial Prospects and Problems,* eds. Prakash, et al.; Oxford & IBH Publishing Co.; New Delhi, India; (1993); and Heslot, et al.; *Molecular Biology and Genetic Engineering of Yeasts;* CRC Press, Inc., U.S.A.; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter, the actin promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. Exemplary promoters for the maize transformation vectors, of the instant invention include any promoter whose expression is specific and limited to endosperm cells. Included are those encoding either 22 kDa zein, opaque2, gamma zein and waxy. Examples of seed-preferred promoters include, but are not limited to, gamma zein promoter and waxy promoter, Boronat, A., Martinez, M. C., Reina, M., Puigdomenech, P. and Palau, J.; Isolation and sequencing of a 28 kDa glutelin-2 gene from maize: Common elements in the 5' flanking regions among zein and glutelin genes; *Plant Sci.* 47:95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18(21):6426 (1990). See the following citation relating to the waxy promoter: Kloesgen, R. B., Gierl, A., Schwarz-Sommer, ZS. and Saedler, H., Molecular analysis of the waxy locus of *Zea mays, Mol. Gen. Genet.* 203:237–244 (1986). An anther specific promoter is 5126 (U.S. Pat. Nos. 5,689,049 and 5,689,051).

The disclosures of each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of sense or antisense nucleic acids to reduce, increase, or alter concentration and/or composition of the proteins of the present invention in a desired tissue. A promoter may be operably linked to the gtf gene, which is followed by the endogenous terminator or the heterogeneous PINII terminator.

The GTF B, GTF C or GTF D protein is directed to the maize endosperm amyloplast using a suitable transit sequence. Transit sequences useful in directing the enzyme into the amyloplast for accumulation within the amyloplast include but are not limited to ribulose biphosphate carboxylase small subunit, waxy, brittle-1, and chlorophyll AB binding protein. The transit sequences are juxtaposed between the promoter and the gtfb, gtfc or gtfd coding sequence and fused in translational reading frame with the gtfb, gtfc or gtfd moiety.

Transit sequences useful in directing the enzyme into the vacuole for accumulation within the vacuole are well known in the art. For vacuolar targeting, see e.g. Ebskamp, et al., "Accumulation of Fructose Polymers in Transgenic Tobacco," *Bio/technology;* Vol. 12; pp. 272–275; (1994); incorporated herein in its entirety by reference.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1, 2, and 6, the Bronze-1 intron are known in the art. See generally, *The Maize Handbook,* Chapter 116, Freeling and Walbot, Eds., Springer, N.Y. (1994).

The vector comprising the sequences from a polynucleotide of the present invention will typically comprise a marker gene that confers a selectable phenotype on plant cells. Usually, the selectable marker gene will encode antibiotic or herbicide resistance. Suitable genes include those coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol. 153:253–277 (1987). Exemplary *A. tumefaciens* vectors useful herein are plasmids pKYLX6 and pKYLX7 of Schardl et al., Gene, 61:1–11 (1987) and Berger et al., *Proc.*

*Natl. Acad. Sci. U.S.A.* 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. U.S.A.* 85:8805–8809 (1988); and Hiatt et al., U.S. Pat. No. 4,801,340.

Another method of suppression is sense suppression. Introduction of nucleic acid configured in the sense orientation has been shown to be an effective means mRNA accumulation of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

PROTEINS

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. U.S.A.* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes modifications that can be made to an inventive protein of without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes, including bacterial hosts such as *Esche-* ricia coli, Salmonella typhimurium, and Serratia marcescens. Eukaryotic hosts such as yeast or filamentous fungi may also be used in this invention. Since these hosts are also microorganisms, it will be essential to ensure that plant promoters which do not cause expression of the polypeptide in bacteria are used in the vector.

Commonly used prokaryotic control sequences include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in E. coli is also useful. Examples of such markers include genes specifying resistance to kanamycin, ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., Gene 22:229–235 (1983); Mosbach, et al., Nature 302:543–545 (1983)).

Synthesis of heterologous proteins in yeast is well known. See Sherman, F., et al., Methods in Yeast Genetics, Cold Spring Harbor Laboratory (1982). Two widely utilized yeast for production of eukaryotic proteins are Saccharomyces cerevisiae and Pichia pastoris. E. coli and P. pastoris are preferred expression systems. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques, enzyme activity assays or radioimmunoassays or other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in The Peptides: Analysis, Synthesis, Biology, Vol. 2: Special Methods in Peptide Synthesis, Part A.; Merrifield, et al., J. Am. Chem. Soc. 85:2149–2156 (1963), and Stewart et al., Solid Phase Peptide Synthesis, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide to Protein Purification, Academic Press (1990). For example, antibodies may be raised to the proteins as described herein. Purification from E. coli can be achieved following procedures described in U.S. Pat. No. 4,511,503. Detection of the expressed protein is achieved by methods known in the art and include for example, radioimmunoassays, Western blotting techniques enzyme activity assays or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises transforming a plant cell with an expression cassette comprising a polynucleotide of the present invention to obtain a transformed plant cell, growing the transformed plant cell under plant forming conditions, and inducing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a non-isolated gene of the present invention to up- or downregulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et aL, PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration or composition is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots or dicots, preferably maize, sugar beet, potato, cassava, sweet potato, soybeans, sunflower, sorghum, canola, wheat, alfalfa, rice, barley and millet.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods include Western blot (immunoblot) analysis, analytical biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an receptor (e.g., streptavidin) molecule that is either inherently detectable or covalently couples to a signal system, such as a detectable enzyme, a fluorescent compound, or a chemiluminescent compound. A number of ligands and receptors can be used. Where a ligand has a natural receptor, for example, biotin, thyroxine, and cortisol, it can be used in conjunction with the labeled, naturally occurring receptors. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495–497 (1975).

Other suitable techniques involve selection of libraries of recombinant antibodies in phage or similar vectors (see, e.g., Huse et al., *Science* 246:1275–1281 (1989); and Ward, et al., *Nature* 341:544–546 (1989); and Vaughan et al., *Nature Biotechnology*, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996). Also, recombinant immunoglobulins may be produced. See, Cabilly, U.S. Pat. No. 4,816,567; and Queen et al., *Proc. Nat'l Acad. Sci.* 86:10029–10033 (1989).

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like.

TRANSFECTION/TRANSFORMATION OF CELLS

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA or a genomic sequence encoding a full length protein, will be used to construct an expression cassette which can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds.

O. L. Gamborg and G. C. Phillips. Springer-Verlag Berlin Heidelberg New York, 1995. U.S. Pat. No. 5,008,200 Ranch et al. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

*Agrobacterium tumefaciens*-meditated transformation techniques are well described in the scientific literature. See, for example Horsch et al., *Science* 233:496–498 (1984), and Fraley et al., *Proc. Natl. Acad. Sci.* 80:4803 (1983). For instance, Agrobacterium transformation of maize is described in U.S. Pat. No. 5,550,318 and WO98/32326 which is incorporated by reference.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. 11, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., Plant Cell Physiol. 25:1353, (1984)), (3) the vortexing method (see, e.g., Kindle, *Proc. Natl. Acad. Sci. U.S.A.* 87:1228, (1990)).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plant Mol. Biol. Reporter, 6:165 (1988). Expression of polypeptide coding genes can be obtained by injection of the DNA into reproductive organs of a plant as described by Pena et al., Nature, 325: 274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

TRANSGENIC PLANT REGENERATION

Transformed plant cells which are derived by any of the above transformation techniques can be cultured to regenerate a whole plant which possesses the transformed genotype. Such regeneration techniques may rely on manipulation of certain phytohormones in a tissue culture growth medium, and on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium can be achieved as described by Horsch et al., *Science*, 227:1229–1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, The Maize Handbook, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenic plants is made and new varieties are obtained and propagated vegetatively for commercial use. In seed propagated crops, mature transgenic plants can be self-pollinated to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard DNA detection techniques. Transgenic lines are also typically evaluated based levels of expression of the heterologous nucleic acid. Expression at the RNA level can be determined initially to identify and quantitate expression-positive plants. Standard techniques for RNA analysis can be employed and include RTPCR amplification assays using oligonucleotide primers designed to amplify only the heterologous RNA templates and solution hybridization assays using heterologous nucleic acid-specific probes. The RNA-positive plants can then be analyzed for protein accumulation by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are screened for the incorporated nucleic acid to identify and select plants with the most appropriate expression profiles.

A preferred embodiment is a transgenic plant that is homozygous for the added heterologous nucleic acid; i.e., a transgenic plant that contains the gene sequence in question at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for copy number of the polynucleotide of the present invention relative to a control plant (i.e., native, non-transgenic). Back-crossing to a parental plant and out-crossing with a non-transgenic plant are also within the scope of the application.

Plants that can be used in the method of the invention include monocotyledonous and dicotyledonous plants. Preferred plants include maize, wheat, rice, barley, oats, sorghum, millet, rye, soybean, sunflower, alfalfa, canola, cotton, potato, sugar beet, cassava, sweet potato, triticale, sugarcane, and transgenic plants thereof.

Seeds derived from plants regenerated from transformed plant cells, plant parts or plant tissues, or progeny derived from the regenerated transformed plants, may be used directly as feed or food, or further processing may occur.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli S. typhimurium,* and *Serratia marcescens.* Eukaryotic hosts such as yeast or filamentous fungi may also be used in this invention. Since these hosts are also microorganisms, it is preferable to ensure that plant promoters which do not cause expression of the protein in bacteria are used in the vector.

The isolated cloning vector will then be introduced into the plant cell using any convenient technique, including bombardment, transformation using Agrobacterium, electroporation (in protoplasts), retroviruses and microinjection into plant cells. Accordingly, a highly preferred embodiment of the present invention is a transformed maize, sugar beet or potato plant, the cells of which contain as foreign DNA at least one copy of the DNA sequence of an expression cassette of the GTF B, GTF C or GTF D protein.

For example, the potato plant can be transformed via *Agrobacterium tumefaciens* to produce the present glucans. The transformation cassette comprises a patatin promoter, followed by the gtfb, gtfc or gtfd coding sequence and the neomycin phosphotransferase polyadenylation site/terminator. See e.g. Utsumi, et al., "Expression and Accumulation for Normal and Modified Soybean Glycinins in Potato Tubers," *Plant Science;* Vol. 102(2); pp. 181–188; (1994); (Limerick); incorporated herein in its entirety by reference. The transgenic cassette is placed into a transformation vector. For example, BIN19, or derivatives thereof, are useful when transforming via *Agrobacterium tumefaciens.* See e.g. Visser, et al., "Transformation of Homozygous Diploid Potato with an *Agrobacterium-tumefaciens* Binary Vector System by Adventitious Shoot Regeneration on Leaf and Stem Segments," *Plant Mol. Biol.;* Vol. 12(3); pp. 329–338; (1989); incorporated herein in its entirety by reference.

For maize transformation and regeneration see e.g. Armstrong, C., (1994), "Regeneration of Plants from Somatic Cell Cultures: Applications for in vitro Genetic Manipulation," *The Maize Handbook,* Freeling, et al. eds, pp. 663–671; incorporated herein in its entirety by reference.

Regenerated putative transgenic plants can be analyzed through PCR and Southern blot analysis using the GTF B, GTF C or GTF D gene as a probe or as template for primers. Northern analysis or RT-PCR can also be performed using RNA isolated from endosperm PCR Protocols: A Guide to Methods and Applications. Academic Press (1990) pp 23–26. M A Innis; D H Gelfand; J J Sninsky; T J White eds. B. A. Larkins, R. A. Jones and C. Y. Tsai (1976). Isolation and in vitro translation of zein messenger ribonucleic acid. Biochemistry. 15, No. 25: 5506–5511.

Once a given transformed plant is identified, the glucans synthesized can be isolated, by standard methods, known to one skilled in the art. B. A. Larkins, C. E. Bracker and C. Y. Tsai (1976). Storage protein synthesis in maize isolation of zein-synthesizing polyribosomes. Plant Physiology. 57: 740–745. B. A. Larkins and C. Y. Tsai (1977). Dissociation of polysome aggregates by protease K1. Plant Physiology. 60: 482–485.

The glucans thus obtained in the transgenic plant can be substituted for modified starches and utilized in the sizing and/or coating steps. For formulations useful in the coating step, see e.g. Heiser, et al., "Starch Formations," *Starch and Starch Products in Paper Coating;* Kearney, et al., eds., pp. 147–162; (1990); Tappi Press; incorporated herein in its entirety by reference.

The present glucans are utilized in an amount of from about 4 to about 15 weight percent, more preferably from about 5 to about 12 weight percent, also preferably from about 6 to about 8 weight percent. Weight percent is defined as grams of molecule per 100 ml coating solution.

The present glucans are used to replace the starch and/or latex molecules completely, or a starch-glucan or a latex-glucan mixture is used in the slurry. In the coating application, the glucan:starch ratio preferably ranges from about 10:90 to about 100:0; more preferably from about 40:60 to about 100:0; more preferably still from about 60:40 to about 100:0; most preferably about 100:0. The glucan:latex ratio preferably ranges from about 10:90 to about 100:0; more preferably from about 40:60 to about 100:0;

more preferably still from about 60:40 to about 100:0; most preferably about 100:0.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Construction of gtf Expression Vectors

The transgene containing the gtf coding sequence was cloned into a plant expression vector. The gamma zein promoter and terminator flanked the coding sequence so as to produce a gtf polypeptide.

Example 2

Transformation

Immature maize embryos were transformed with the gtf expression vectors described above using standard maize particle bombardment and Agrobacterium-mediated transformation methods as described. Plants were regenerated using standard techniques.

Neither T0 nor T1 plants exhibited any deleterious effects upon their health that were significantly different from any other plant derived from regeneration from tissue culture. Seed set was normal and plant height and overall health was normal.

Example 3

Southern Blot Analysis

Southern blots on DNA isolated from transgenic T2 seed from T1 plants were performed essentially by the method described in "Molecular Cloning" Eds. J, Sambrook, E. F. Fritsch and T. Maniatis, Cold Spring Harbor Laboratory Press, 1989. The Plant Transcription Unit (PTU) Analysis and Integration Analysis were performed by probing Southern blots of DNA digested to display the intact PTU. Or in the case of integration analysis, blots were digested with enzymes with recognition sites not present at the ends of the PTU to demonstrate unique integration patterns.

These results demonstrate that the DNA containing the gtf gene was stably integrated into the maize genome of GS3 and that each independent transformation event exhibited at least one gtf transcriptional unit. Southern blots of T2 seed from T1 plants demonstrate the presence of at least eight independent stable transformation events in GS3 for gtfc.

DNA containing the gtfc gene was stably integrated into the maize genome of the same transgenic GS3 events described above. Furthermore, unique DNA integration patterns indicate that each event is derived independently. Southern blots of T2 seed from T1 plant show at least seven independent stable transformation events in GS3 for gtfc.

Example 4

RT-PCR Reverse Transcriptase Polymerase Chain Reaction

RT-PCR was performed by the method described in PCR Protocols: A Guide to Methods and Applications. Academic Press (1990) pp 23–26. M A Innis; D H Gelfand; J J Sninsky; T J White eds. The following method was used to isolate mRNA:

Dissected embryo from the seed and discarded embryo;
Pooled the 10 seeds and pulverized the kernel to flour;
Weighed 50-mg kernel meal per sample and 50-mg GS3 kernel meal;
Resuspended each in 300-$\mu$l 50 mM MOPS, pH 7.0 by vortexing;
Added to each sample 100-$\mu$l $\alpha$-amylase solution (770 units/mg, heat stable, prepared by dissolving 1.0 mg in 1.4-ml 50 mM MOPS, pH 7.0);
Carried out the digestion in a 85° C. water bath for 1 h with periodic vortexing;
Added to the reaction 1.2-ml methanol, kept at −20° C. for 10 min, and centrifuged in at 15K for 10 min;
Decanted and washed the pellet with 1.0-ml 70% methanol;
Reverse Transcriptase PCR (RT-PCR) of mRNA isolated form gtfc transgenic maize was performed using PCR primers near the 5' end and within the gtfc coding sequence were used on mRNA isolated from GS3, T2 seed.

The RT-PCR bands indicate expression of the transgene in T2 seed in at least seven independent stable transformation events in GS3 for gtf-c.

Primer pairs include:
position 115-386: ACAGCAACTTCAGCAACATCT-CAAC and GACGGCTGTTTTAATTTACCAATCT
position 144-400: CGCCACTGTTACTGATMT-GTTTCT and CTTGACTAAGTGATGACGGCT-GTTT

Example 5

Evaluation of Soluble Glucans

Transgenic plants expressing glucosyltransferase were used to isolate soluble glucans. The gtfd glucans produced by mutant N471D were evaluated and the results are shown in the following table.

| EVALUATION OF SOLUBLE GLUCANS | | |
|---|---|---|
| Starch I.D. | N471D (2%) | Pen Gum 280 (9%) |
| Rod Number | 9 | 7 | 9 |
| Starch Pick-up (#/3300 sq. ft.) | 1.04 | 2.01 | 2.51 |
| HST (sec.) | 1.1 | 1.9 | 2.3 |
| G. Stiffness | | | |
| CD | 65 | 75 | 64 |
| MD | 135 | 135 | 143 |
| IGT Pick v.v.p. | 110 | 187 | 193 |
| G. Porosity cc. | 30 | 17 | 12 |

*HST is a size test, the larger the number the more sizing the paper gets.
*IGT pick is a test for paper surface strength, the higher the number the better.
*G. porosity is a test for the porosity of the paper. The lower the number the tighter the paper, it also means the better the film formed by the starch.

Example 6 gtfb and gtfd Mutants

Gtfb and gtfd mutants were generated by site directed mutagenesis as well known in the art. The nomenclature used to identify the mutant enzymes used to produce the present glucans is described above.

Site-directed mutagenesis of gtfb resulted in mutant GTF B enzymes having changes at positions I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; K779Q; K1014T and D567T/D571K/K1014T.

Site-directed mutagenesis of gtfd resulted in mutant GTF D enzymes having changes at positions T589D; T589E; N471D; N471D/T589D; and N471D/T589E.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

I claim:

1. A method of manufacturing paper comprising adding a glucan to one or more steps in paper manufacturing, wherein the glucan is synthesized by a glucosyltransferase B or glucosyltransferase D enzyme, wild-type or mutant.

2. The method of claim 1 wherein the glucan is added to a wet end, sizing or coating step.

3. The method of the claim 2 wherein the glucan is added to a coating step.

4. The method of claim 3 wherein the amount of glucan utilized is from about 4 to about 15 weight percent of the slurry used in the coating application.

5. The method of claim 4 wherein the amount of glucan utilized is from about 5 to about 12 weight percent of the slurry used in the coating application.

6. The method of claim 1 wherein the glucan is produced by a glucosyltransferase B mutant having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q.

7. The method of claim 6 wherein the glucosyltransferase B mutant has changes at positions I448V; I448V/D457N/D567T/D571K/K779Q/K1014T or Y169A/Y170A/Y171A.

8. The method of claim 7 wherein the glucosyltransferase B mutant has a change at position I448V.

9. The method of claim 1 wherein the glucan is produced by a glucosyltransferase D wild-type or a mutant having changes at positions selected from the group consisting of T589D; T589E; N471D; N471D/T589D; and N471D/T589E.

10. The method of claim 9 wherein the glucosyltransferase D mutant has a change at N471D.

11. The method of claim 10 wherein the glucosyltransferase D mutant is used paper sizing or coating.

12. A method of imparting gloss on paper during the manufacturing process comprising adding a glucan to a coating step, wherein the glucan is synthesized by a glucosyltransferase B or glucosyltransferase D enzyme, wild-type or mutant.

13. The method of claim 12 wherein the amount of glucan utilized is from about 4 to about 15 weight percent of the slurry used in the coating application.

14. The method of claim 13 wherein the amount of glucan utilized is from about 5 to about 12 weight percent of the slurry used in the coating application.

* * * * *